(12) United States Patent
Tranquillo et al.

(10) Patent No.: US 6,666,886 B1
(45) Date of Patent: Dec. 23, 2003

(54) TISSUE EQUIVALENT APPROACH TO A TISSUE-ENGINEERED CARDIOVASCULAR VALVE

(75) Inventors: Robert T. Tranquillo, Arden Hills, MN (US); Timothy S. Girton, Maple Grove, MN (US); Michael Neidert, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/505,121

(22) Filed: Feb. 16, 2000

Related U.S. Application Data
(60) Provisional application No. 60/120,167, filed on Feb. 16, 1999.

(51) Int. Cl.[7] .................................................. A61F 2/06
(52) U.S. Cl. ...................................... 623/2.42; 623/2.12
(58) Field of Search ............................... 623/2.12–2.16, 623/2.42

(56) References Cited

U.S. PATENT DOCUMENTS

| | | | | |
|---|---|---|---|---|
| 5,558,875 A | * | 9/1996 | Wang .......................... | 424/422 |
| 5,759,830 A | | 6/1998 | Vacanti et al. ............... | 435/180 |
| 5,770,417 A | | 6/1998 | Vacanti et al. ............... | 435/180 |
| 5,855,601 A | * | 1/1999 | Bessler et al. .............. | 623/2.38 |
| 5,899,937 A | * | 5/1999 | Goldstein et al. ............... | 623/2 |
| 5,910,170 A | * | 6/1999 | Reimink et al. ........... | 623/2.38 |
| 5,948,654 A | * | 9/1999 | Tranquillo et al. ........... | 435/174 |
| 5,994,123 A | | 11/1999 | Olszewski et al. ........ | 435/320.1 |
| 6,146,892 A | * | 11/2000 | Ma et al. ..................... | 264/45.6 |

OTHER PUBLICATIONS

Barocas, V.H., et al., "An Anistrophic Biphasic Theory of Tissue–Equivalent Mechanics: The Interplay Among Cell Traction, Fibrillar Network Deformation, Fibril Alignment, and Cell Contact Guidance", *Journal of Biomechanical Engineering, 119*, pp. 137–145, (May 1997).

Barocas, V.H., et al., "Engineered Alignment in Media Equivalents: Magnetic Prealignment and Mandreal Compaction", *Journal of Biomechanical Engineering, 120*, pp. 660–666, (Oct. 1998).

Christie, G.W., "Anatomy of Aortic Heart Valve Leaflets: The Influence of Glutaraldehyde Fixation on Function", *European Journal of Cardio–thoracic Surgery, 6 (12), Suppl. 1*, pp. S 25–S33, (1992).

Girton, T.S., et al., "Exploiting Glycation to Stiffen and Strengthen Tissue Equivalents for Tissue Engineering", pp. 87–92, (May 5, 1999), http://www3.interscience.wiley.com/cgi–bin/issuetoc?ID=61004825.

Gottlob, R., et al., *Venous Valves*, Springer–Verlag, Wein, pp. 1–227, (1986).

L'Heureux, N., et al., "In Vitro Construction of a Human Blood Vessel from Cultured Vascular Cells: A Morphologic Study", *Journal of Vascular Surgery, 17 (3)*, pp. 499–509, (Mar. 1999).

Sapatnekar, S., et al., "Blood–biomaterial interaction in a flow system in the presence of bacteria: Effect of protein adsorption", *Journal of Biomedical Materials Research, 29*, pp. 247–256, (1995).

(List continued on next page.)

*Primary Examiner*—Corrine McDermott
*Assistant Examiner*—Thomas Barrett
(74) *Attorney, Agent, or Firm*—Schwegman, Lundberg, Woessner & Kluth, P.A.

(57) ABSTRACT

The invention provides a molded valve leaflet containing a molded biopolymer having fibrils and cells within the molded biopolymer, wherein the fibrils of the molded biopolymer have commisure-to-commisure alignment. The invention also provides a valve equivalent containing a plurality of molded valve leaflets that are connected to a base, wherein the molded valve leaflets include a molded biopolymer having fibrils and cells within the molded biopolymer, wherein the fibrils of the molded biopolymer have commisure-to-commisure alignment.

15 Claims, 10 Drawing Sheets

OTHER PUBLICATIONS

Sauren, A.H., et al., "Aortic Valve Histology and its Relation with Mechanics–Preliminary Report", *Journal of Biomechanics, 13* (2), pp. 97–104, (1980).

Sauren, A.H., et al., "The Mechanical Properties of Porcine Aortic Valve Tissues", *Journal of Biomechanics, 16* (5), pp. 327–337, (1983).

Shinoka, T., et al., "Tissue Engineering Heart Valves: Valve Leaflet Replacement Study in a Lamb Model", *Supplement to The Annals of Thoracic Surgery, 60* (6) *Suppl.*, pp. S513–S516, (Dec. 1995).

Talman, E.A., et al., "Internal Shear Properties of Fresh Porcine Aortic Valve Cusps: Implications for Normal Valve Function", *J. Heart Valve Dis., 5* (2), pp. 152–159, (1996).

* cited by examiner ns a gap between the top and bottom mandrel pieces.
TISSUE EQUIVALENT APPROACH TO A TISSUE-ENGINEERED CARDIOVASCULAR VALVE This application claims the benefit under 35 U.S.C. §119(e) of U.S. Provisional Patent Application No. 60/120,167, filed Feb. 16, 1999, which is hereby incorporated by reference.

TECHNICAL FIELD OF THE INVENTION

The present invention pertains generally to substitute heart valves, and more particularly to tissue-engineered cardiovascular valves.

BACKGROUND

The introduction of substitute heart valves (SHV's) into clinical practice in the 1960's resulted in a dramatic improvement in the longevity and symptomatology of patients with valvular heart disease. However, major problems remain. With the exception of autograft and allograft aortic valves and repaired mitral valves, the 10-year mortality after valve replacement with either mechanical or bioprosthetic valve ranges between 30 and 55 percent. The incidence of thromboembolic complications is 1.5–3.0 per 100 patient-years (percent/year); prosthetic valve endocarditis averages approximately 0.5 percent/year. The incidence of bleeding complications is 1.5–3.0 percent/year for anticoagulated patients and approximately one-third that rate for patients who are not anticoagulated. The reoperation rate ranges between 2 and 4 percent/year; by 10 years one-third of bioprosthetic valves require replacement and by 15 years more than two-thirds do. Autografts and allograft aortic valve substitutes have limited availability and require longer and more complicated surgery; therefore, these valve substitutes are prescribed for younger patients, generally below age 60. Mitral valve repair is helpful in approximately two-thirds of patients, but often is less suitable for older patients and decreases but does not eliminate the morbidity of bioprosthetic valves. These data loudly announce and convincingly certify that SHV's developed and approved for clinical use 15–30 years ago replace one disease with another and are far from ideal.

Better SHV's that can be quickly and safely implanted in older patients who often have comorbid disease are needed. Incremental improvements in existing mechanical and bioprosthetic heart valves may help, but visionary new designs and new approaches that specifically address the complications of reduced lifespan, thromboembolism, the need for anticoagulation, endocarditis and structural deterioration are more appropriate goals for our biotechnical effort. New biomaterials and surface coatings, new mechanical valve designs, longer lasting hemodynamically normal xenografts and tissue-engineered valves from autologous cells are some of the new ideas for developing an ideal heart valve substitute.

Development of truly new SHV's requires a multidisciplinary approach, spanning clinical science, cell and molecular biology, materials science and bioengineering. Although much is known regarding the mechanisms of thromboembolism, endocarditis, structural deterioration and other morbid events, much more basic information is needed before a SHV becomes a "cure."

Thus, while mechanical and bioprosthetic heart valves (mhv and bhv) have made a dramatic impact since their introduction in the 1960's, the 10-year mortality after replacement is relatively high, with undesirable reoperation rates because of mechanical failure (mhv), bleeding and thromboembolic complications (mhv and bhv), and calcification (bhv). Autografts and allografts, while more successful, fall far short in supply. The need is particularly great for juveniles since neither mhv nor bhv have the capacity to grow. Thus, there is great interest in developing a new generation of substitute heart valves based on tissue-engineering approaches (1).

SUMMARY OF THE INVENTION

We have developed a mold to fabricate multileaflet "valve-equivalents" based on the tissue-equivalent approach of entrapping tissue cells in a self-assembled biopolymer scaffold. The mold design results in leaflet structures possessing circumferential alignment of protein fibers characteristic of native leaflets. Accordingly, the present invention provides method and apparatus for forming one or more substitute valve leaflets from a solution of fibrillar biopolymer gel and tissue cells, wherein there is provided a female surface and a male surface adapted to cooperate with the female surface to define a compaction volume therebetween for receiving the solution, wherein the method and apparatus is adapted to produce one or more contiguous substitute valve leaflets having structural alignment and mechanical properties which mimic those of natural valve leaflets.

BRIEF DESCRIPTION OF THE DRAWINGS

FIG. 4 illustrates a two-dimensional comparison between an engineered valve equivalent and a natural aortic valve indicating that the basic geometry and dimensions are comparable.

8: gap between the top and bottom mandrel piece that determines the geometry of the individual leaflets. 9: divider wall that separates individual leaflets. 10: edge to which the biopolymer is anchored to the artifical root such that constrained cell-driven compaction of the gel results in commisure-to-commisure orientation. 11: gap between the mandrel and the wall that defines the artificial aortic root or vein section. 12: central groove that allows for leaflet compaction and coaptational surface.

DETAILED DESCRIPTION

In the following detailed description, reference is made to exemplary embodiments in which the invention may be practiced. The reader is referred to the accompanying drawings which form a part of the description hereof, and in which are shown by way of illustration specific embodiments in which the invention may be practiced. Those skilled in the art will recognize that many embodiments are possible within the scope of the invention. Variations, modifications, and combinations of the various embodiments can certainly be made and still fall within the scope of the invention.

Figure 1:
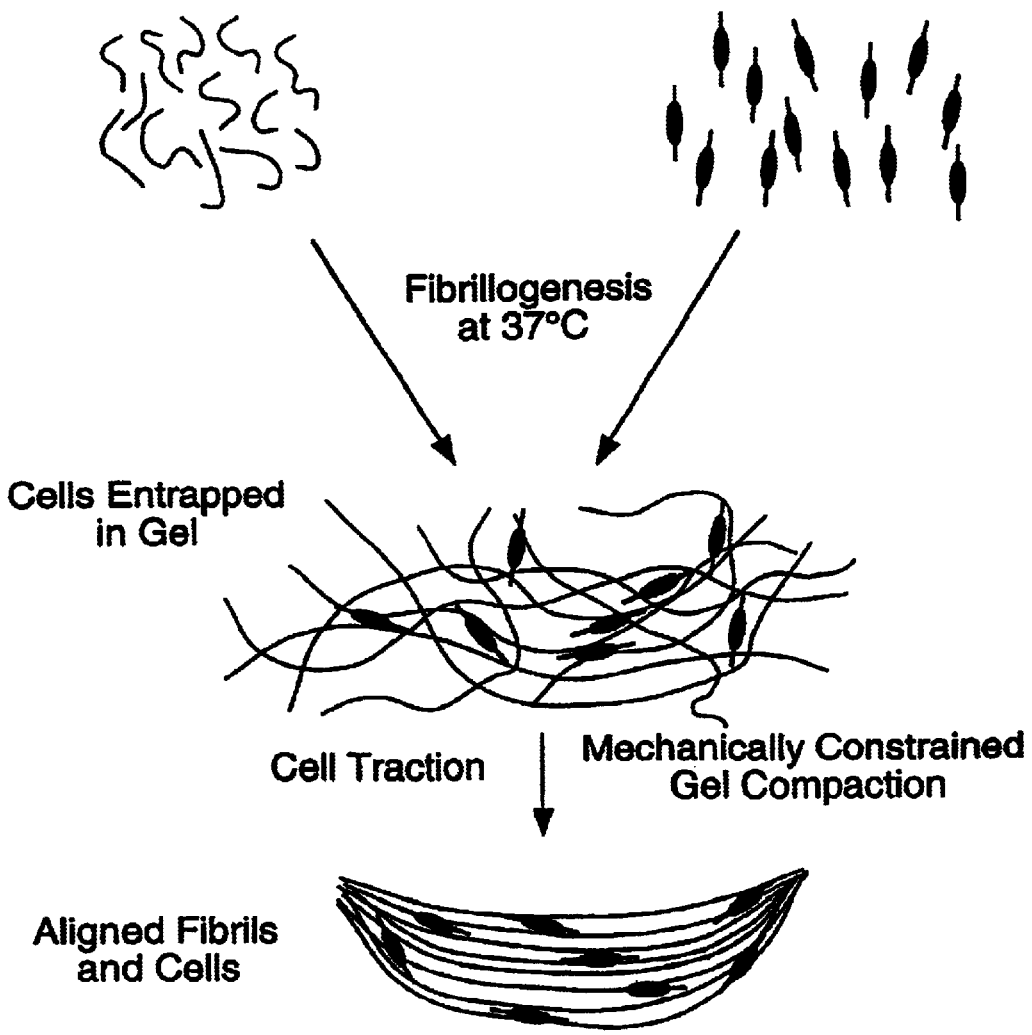
FIG. 1 illustrates an example overview of a process for forming an engineered tissue equivalent.

The invention described herein provides a mold for forming a tissue-engineered cardiovascular valve that allows a multileaflet valve to be formed, and yields leaflets with circumferential alignment of the collagen (or fibrin) fibrils after the cells compact the gel. The alignment mimics the native alignment and provides a "template for remodeling" in vitro and upon implantation. One embodiment of a basic process for forming a tissue equivalent material is illustrated in FIG. 1.

The invention is also directed to a tissue-engineered, multileaflet valve and a method of making the valve.

| Definitions |
|---|
| ECM — Extra-Cellular Matrix |
| FBS — Fetal Bovine Serum |
| DMEM — Dulbecco's Modification of Eagle's Medium |

Knowledge of how mold design determines the evolving structure of a tissue-equivalent formed within (tissue-equivalent meaning reconstituted type I collagen gel with entrapped cells) will be used to create leaflets and, ultimately, a complete heart valve. In particular, the transverse (a.k.a. circumferential) alignment of collagen structures in the major fibrous layer of the leaflet (fibrosa) should be attainable with a triangular mold made of a nonadhesive material (e.g., Teflon) except for the base, which would be composed of material that anchors the tissue-equivalent as the entrapped fibroblasts (possibly but not necessarily produced by cell culture of fibroblasts of heart valve origin) compact the tissue-equivalent. The mechanical properties of the leaflet can be modulated by propitious choice of the culture conditions which modulate cell ECM synthesis and ECM crosslinking.

Figure 2:
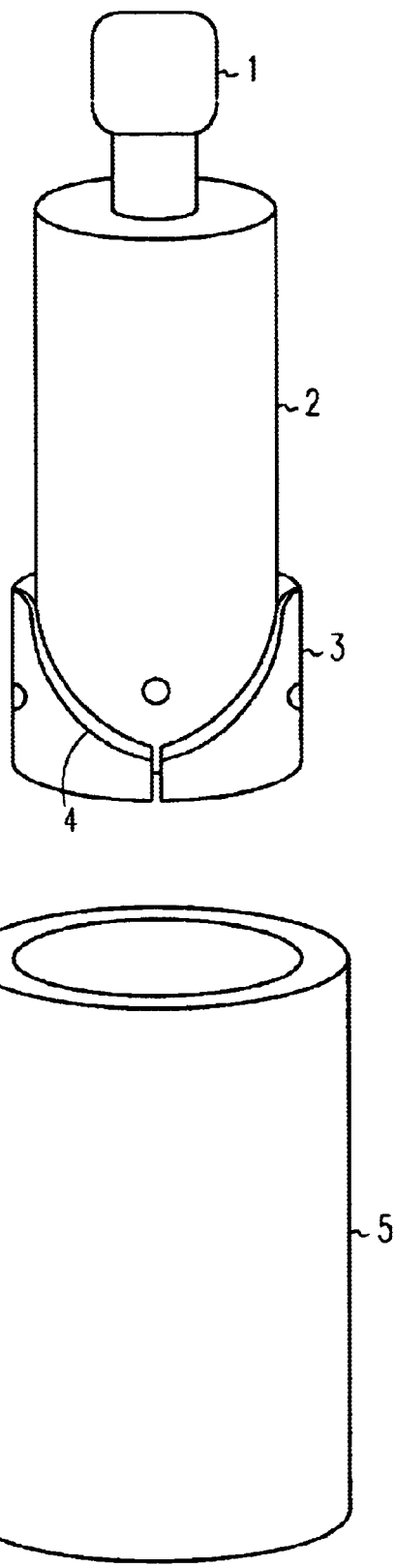
FIG. 2 illustrates an example embodiment of a mold for forming an engineered tissue equivalent valve. 1: handle to allow removal of mandrel from cup. 2: non-adhesive teflon mandrel. 3: teflon horns to define leaflet geometry. 4: porous PE strips to anchor gel fibrils to horns to generate circumferential alignment characteristic of native leaflets. 5: polycarbonate cup.
Figure 3:
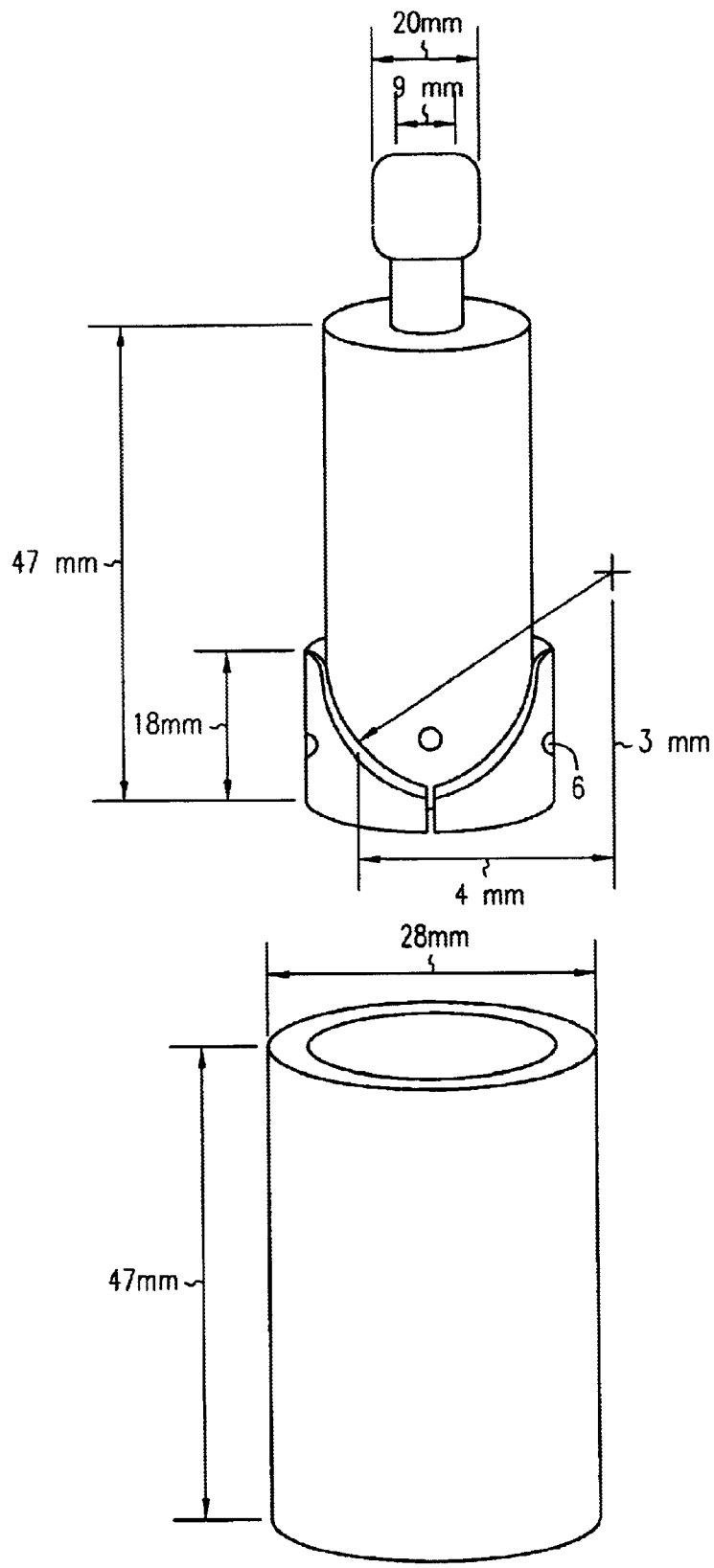
FIG. 3 illustrates the dimensions of an example embodiment of a mold for forming an engineered tissue equivalent valve. 6: two holes at 180° apart for venous valve equivalent, three holes at 120° apart for heart value equivalent.

It is envisioned that the basic structure of a complete heart valve can be attained by a direct extension of the mold described above that will form multiple leaflets continuous with an aortic ring. An example embodiment of a mold as described is illustrated in FIGS. 2 and 3.
Valve Equivalent (VE) Fabrication
Preparation of Cells Dermal fibroblasts are obtained from 6–8 week old Fisher rats. Two cm² pieces of skin are excised from the thigh area of the rats, minced, and placed in 20% FBS supplemented DMEM. Cells are cultured in low glucose DMEM supplemented with 1% Penicillin/Streptomycin and 10% FBS on poly(ethylene terephthalate) tissue culture flasks (In Vitro Scientific). Cell cultures are incubated at 10% $CO_2$ and passed at confluency. Cell cultures do not exceed pass ten.
Preparation of Collagen Solution Collagen solution is prepared from Vitrogen 100 (Collagen Corp.) at a concentration of 3.3 mg/ml. Collagen solution is then seeded with rat dermal fibroblasts at a concentration of $1 \times 10^6$ cells/ml. Alternatively, a fibrin solution prepared by combining fibrinogen and thrombin (R&D Systems) with cell suspension solution is used instead of collagen solution.
Preparation of Valve Equivalent Molds The valve equivalent (VE) mold consists of surfaces that define the valve and leaflet geometry (the "horns") and a region that provides extra volume to allow for significant cell-induced compaction of the collagen gel. Strips of porous polyethylene are attached to the leaflet horns to serve as anchor points which confine compaction of the gel inducing the desired fiber orientation. The geometry of the gel is defined by the non-excluded volume defined by the mandrel, cup, and O-ring (fitted over the top of the mandrel). Before placing the mandrel into the cup, the mandrel is coated with a thin layer of Vaseline™ to ensure uniform compaction. The collagen solution is slowly injected via syringe through the O-ring into the mold. Extreme care must be taken to avoid the formation of air bubbles which may create voids in the resulting valve equivalent. The collagen solution is incubated at 37° C. for five hours during which time gelation occurs and cells become entrapped between collagen (or fibrin) fibers. In order to avoid cell settling during this time, the mold is flipped at 10 minute intervals to ensure a uniform cell distribution. After gelation has occurred, the mandrel (with the surrounding collagen gel) is removed from the cup and placed into Medium 199 supplemented with 10% FBS, 5% L-glutamine, 5% penicillin/streptomycin, and 5% Fungizone.
Valve Equivalent Incubation The construct is incubated under static conditions at 37° C. for 4–10 weeks. The medium is changed once every week. Depending on the desired experimental conditions, the medium is replaced with supplemented medium (e.g., ribose to promote glycation and associated cross-linking). Alternatively, the valve equivalent can be incubated under cyclic loading conditions in which the leaflet "horns" with the attached collagen gel are removed from the central mandrel and placed in a pulsatile flow loop.
Removal of Valve Equivalent from Mold The VE is removed from the mold by first removing the "horns" from the central mandrel. The attached edges of the VE are then cut from the porous polyethylene with a scalpel blade.
A Tissue-Engineered Heart Valve ("Valve-Equivalent")

Considered in its most basic form, the heart valve comprises 2–4 leaflets (depending on the valve type) attached to a fibrocartilaginous ring at the base. It is known that the proper regulation of blood flow through the valves during the cardiac cycle depends on the leaflets having the appropriate tensile and bending properties so that they "open" and "close" to the proper extent under normal arterial pressure and flow swings (2). The leaflets are comprised of three layers: the fibrosa is primarily collagen with some elastin, having large fiber bundles being highly aligned in the circumferential (lateral) direction (3)—it is the main load-carrying structure; the spongiosa is primarily glycosaminoglycans and water, having loose connections between it and the outer fibrosa and ventricularis layers—it permits shearing between layers; the ventricularis contains more elastin than the fibrosa, is less organized, and about half the thickness (0.2 mm). Myofibroblasts are the main cellular type within the leaflet, although their disposition has been little studied. The leaflet is covered by an endothelium. The italicized text is meant to emphasize the important structure-function relation that should be mimicked in a tissue-engineered valve in order to provide a template for remodeling by the host into native tissue with appropriate mechanical properties.

While this situation suffices to warrant the proposed development of the tissue-engineered heart valve, there is a much larger clinical need for a low-cost venous valve replacement. Venous valves in the legs play a key role in distributing pressure throughout the body and maintaining blood flow to the heart. They generally possess two leaflets of similar shape and structure as heart valves leaflets, and so will not be detailed further here. Venous valves frequently become incompetent, particularly when the veins become stretched due to venous hypertension and chronic venous insufficiency in which case the leaflets cannot completely close the valve. The consequent loss of pressure compartmentalization causes an increase in venous pressure leading to edema and reduced blood flow rate (with increased risk of thrombosis), as well as further stretching and valvular incompetence. Given the prevalence of these conditions, especially in an aging population, the clinical need and potential market for a low-cost venous valve replacement is indeed very large.

To date, there has only been one published report of a tissue-engineered heart valve leaflet, which was based on seeding autologous cells onto polyglactin woven mesh (4). While the leaflet was functional when sutured into a lamb heart valve based on echocardiography, histologic examination revealed they were thicker and less flexible. And while there was some resemblance of normal cellular organization, the extracellular matrix was not well developed with evidence of an inflammatory reaction. We are not familiar with any published reports of a tissue-engineered heart valve or venous valve.

An attractive alternative to synthetic biodegradable polymers like polyglactin for soft tissue replacements is the biopolymer type I collagen. In addition to being a native cell substrate and relatively information-rich, cellularity can be achieved directly by cell entrapment during fibillogenesis. An even more attractive alternative is the biopolymer fibrin, which appears to promote matrix remodeling and cell growth in vitro. "Tissue-equivalents" prepared from these fibrillar biopolymers have the further advantage that the fibrils can be aligned by appropriate constraint of the subsequent cell-induced compaction of the gel. We have confirmed the report by Auger (5) that collagen-based tissue-equivalent tubes, or media-equivalents (MEs) with strong circumferential alignment can be fabricated by constraining the compaction by placing a nonadhesive mandrel through the lumen (6). More importantly, we have also developed a theory that predicts this effect (7) and can be used to guide the mechanical constraint required to achieve the desired alignment in any geometry, in particular, the circumferential alignment characteristic of the mechanically significant fibrosa of the leaflets. Further, we have shown that collagen cross-linking via glycation should be useful as a means to modulate the mechanical stiffness of the valve equivalents (VEs) since it is tolerated by the cells (8). Since glycation nonenzymatically cross-links any proteins with free amine groups, it should be a valuable approach with fibrin-based VEs as well. Thus, we have developed a set of tools that are relevant for development of a VE.

Figure 4A:
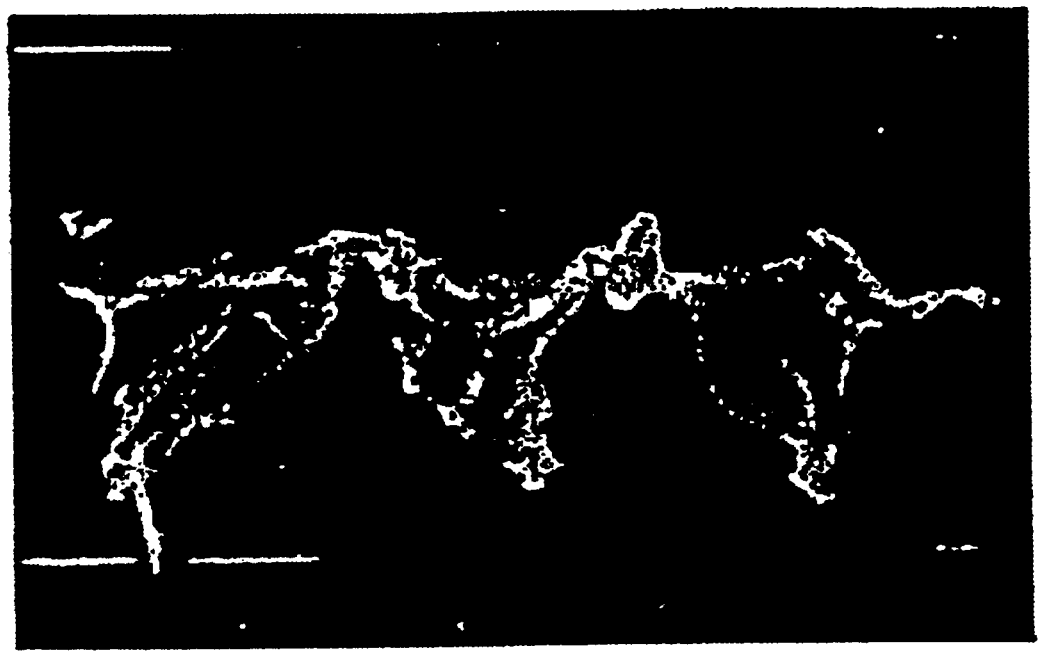
FIG. 4A: valve equivalent.
Figure 4B:
FIG. 4B: natural aortic valve (Thubrikar).
Figure 5:
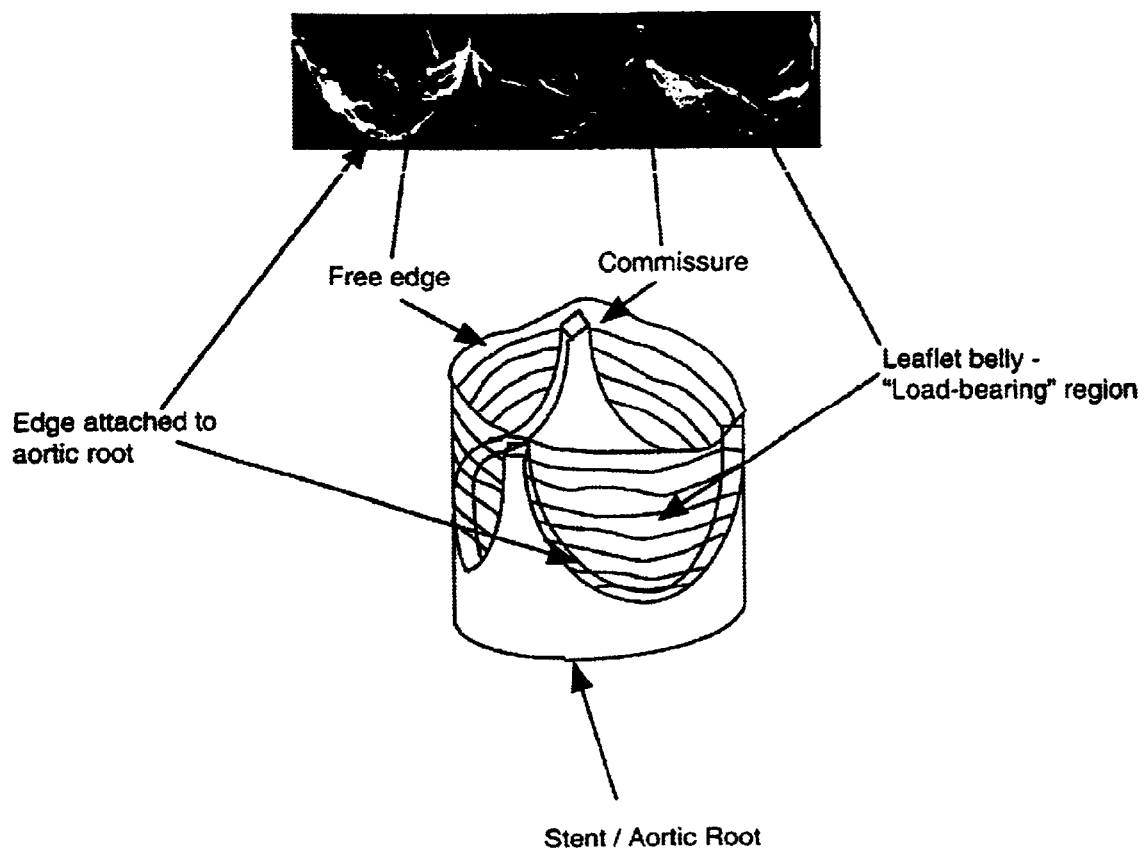
FIG. 5 illustrates the two-dimensional (top panel) and three-dimensional (bottom panel) geometry of natural valves and valve equivalents.
Figure 6:
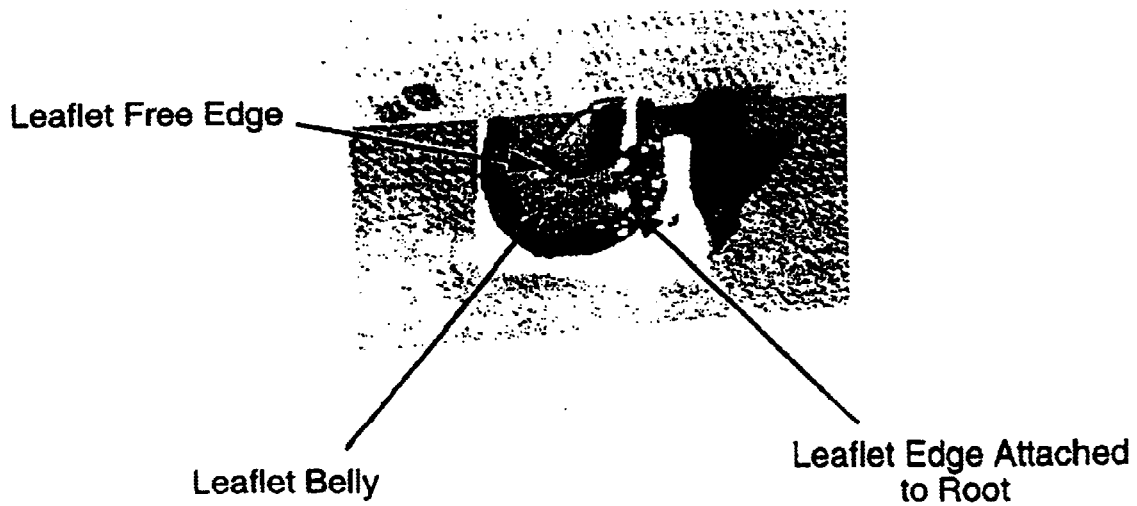
FIG. 6 illustrates a stent mounted engineered tissue equivalent valve.
Figure 7:
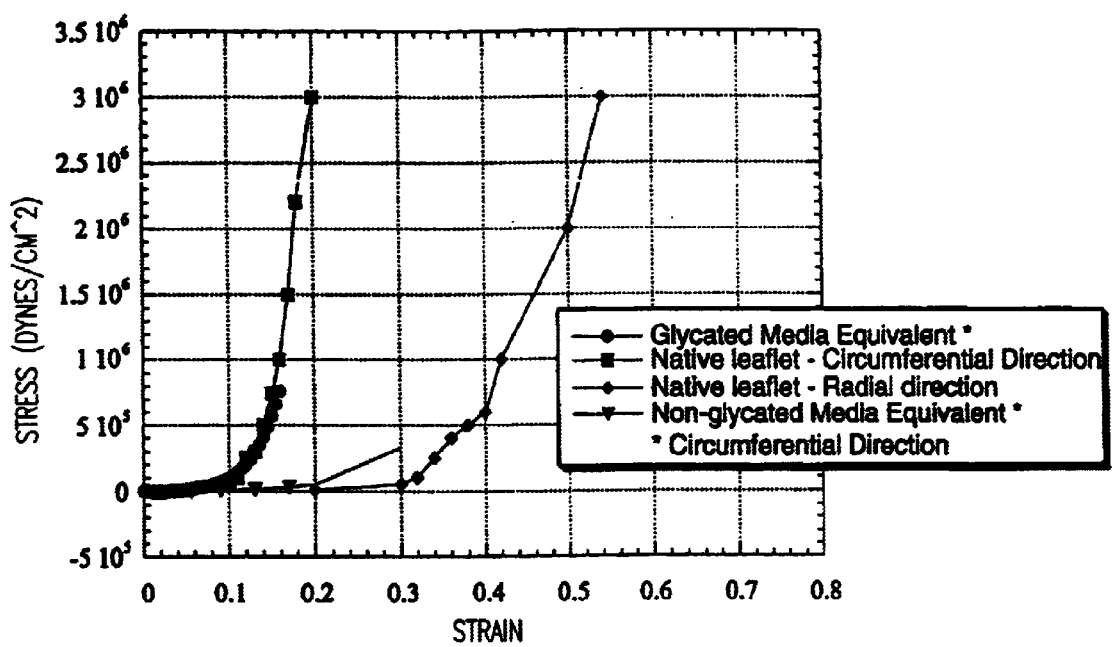
FIG. 7 illustrates a comparison of a tissue equivalent and natural valve with respect to stress-strain properties.
Figure 8:
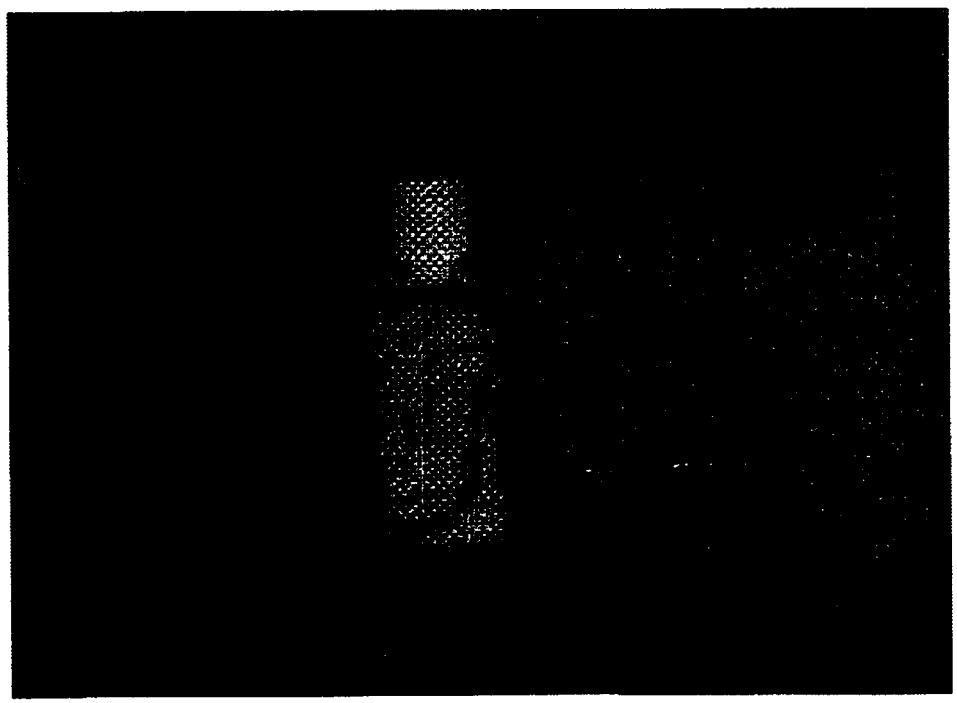
FIGS. 8, 9 and 10 illustrate views of a mold according to one example embodiment of the invention.
Figure 9:
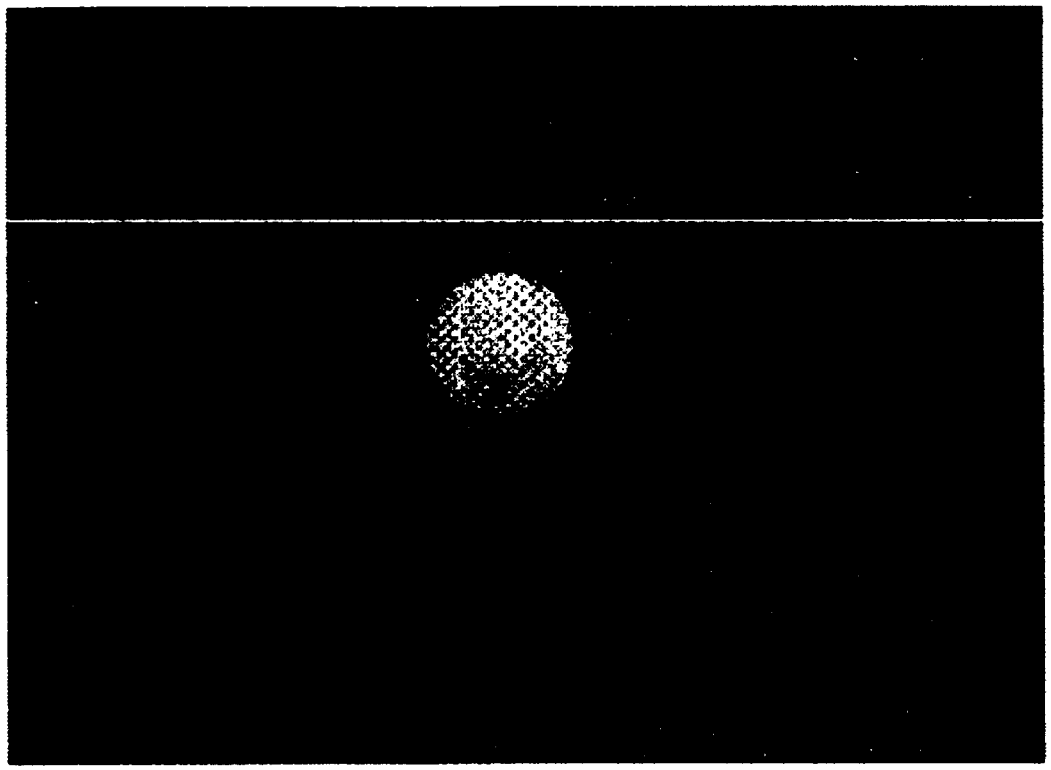
Figure 10:
Figure 11:
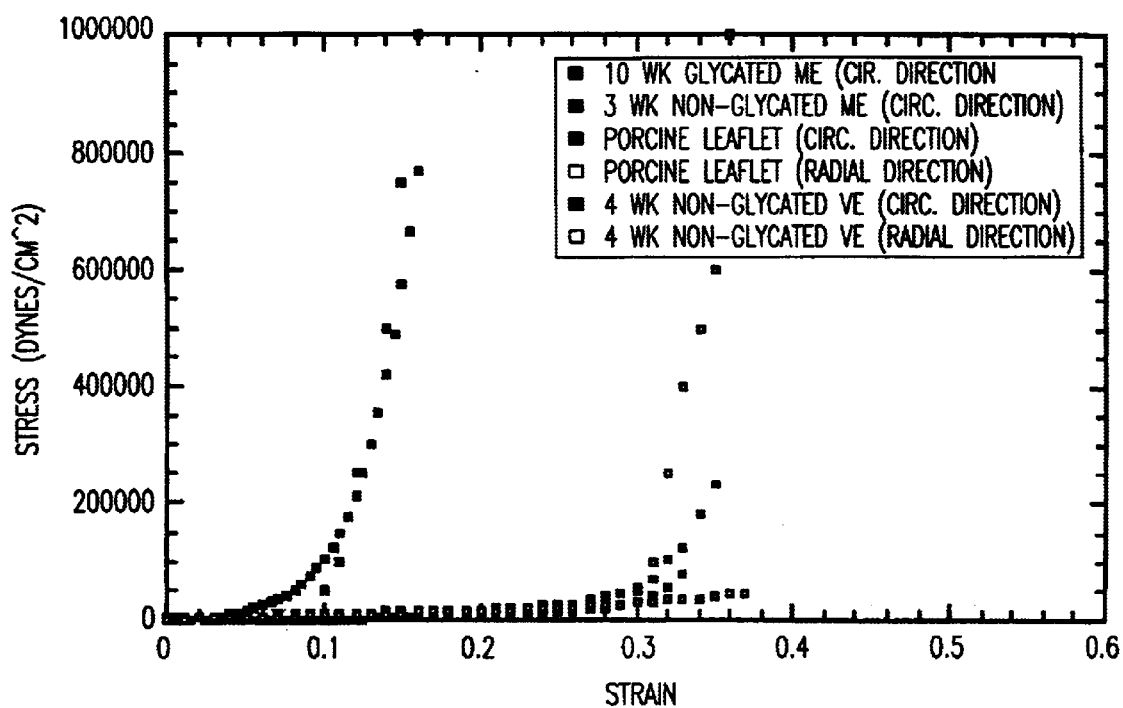
FIG. 11 illustrates a stress-strain curve comparison of tissue equivalent, natural valve leaflet, and a media equivalent.

Referring to FIGS. 4 and 5 there is illustrated a comparison between a VE and a natural aortic valve. Referring to FIG. 6 there is illustrated a stent mounted VE. Referring to FIG. 7, there is illustrated a mechanical stress-strain comparison of a VE and a natural valve. Referring to FIGS. 8, 9 and 10 there is illustrated views of the VE mold according to one example embodiment. Referring to FIG. 11 there is shown a stress-strain plot: anisotropic properties of the VE leaflets are evident as for published data for native leaflets (i.e., stiffer for the circumferential direction). The comparison to our media-equivalent data (similarly fabricated tubes) suggest that with longer incubation times, the VE leaflets will stiffen so that the stress-strain curves will exhibit approximately the desired stiffness as well as the anisotropy.

Figure 12:
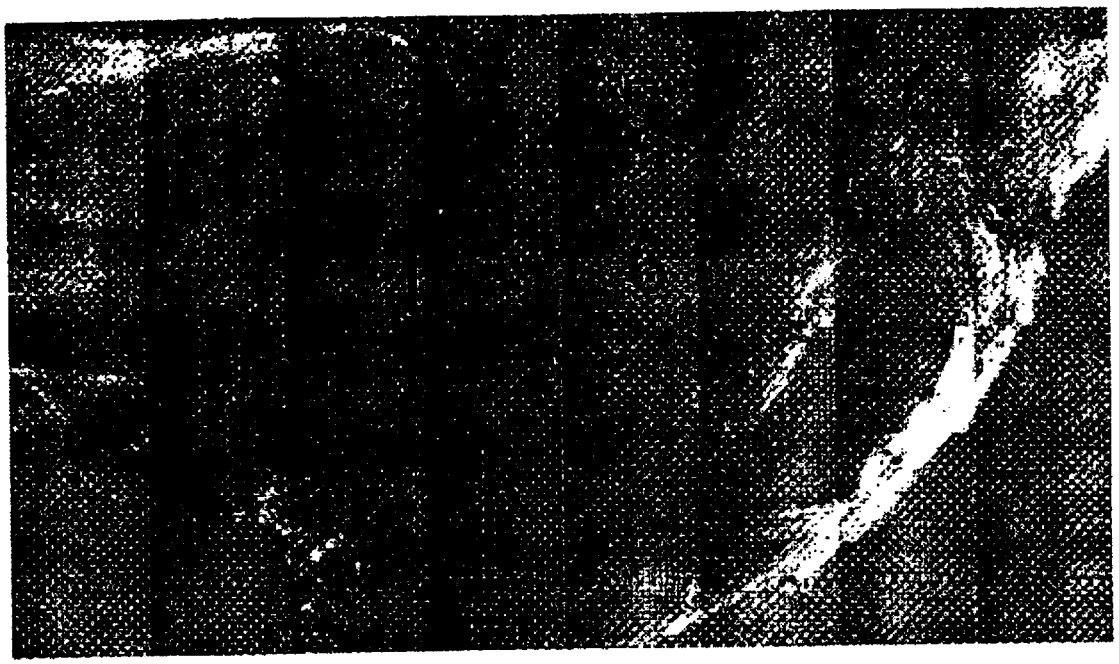
FIG. 12 illustrates a birefringence map of a representative valve equivalent leaflet showing the fiber orientation in the leaflet. The value chi is shown on the leaflet and indicates the angle of orientation.

Other data for the leaflets that were mechanically tested:
4 wk nonglycated VE leaflets from type I collagen and rat dermal fibroblasts (n=3):
thickness: 0.61+/−0.08 mm
cell number: 0.86+/−0.07×106 cells/ml
cell viability: 88+/−5%
commissure height: 1.0+/−0.2 mm Referring to FIG. 12 there is illustrated an image of a birefringence map of a representative valve equivalent leaflet, which indicates the direction and magnitude of collagen fibril alignment as measured by birefringence for a representative leaflet.

An O-ring is provided on the mandrel to contain the collagen solution in the early phases of gelation. Basically, we have to flip the mold a number of times during gelation to ensure a uniform cell distribution. Without the O-ring, the collagen solution would simply leak out of the mold. Also, an added feature shown in the photographs is a velcro slab on top of the Teflon "horn." This piece serves to anchor the collagen to provide sufficient height for the commissure. Without this anchor, the collagen will compact all the way down to the surface of the "horn."

Figure 13:
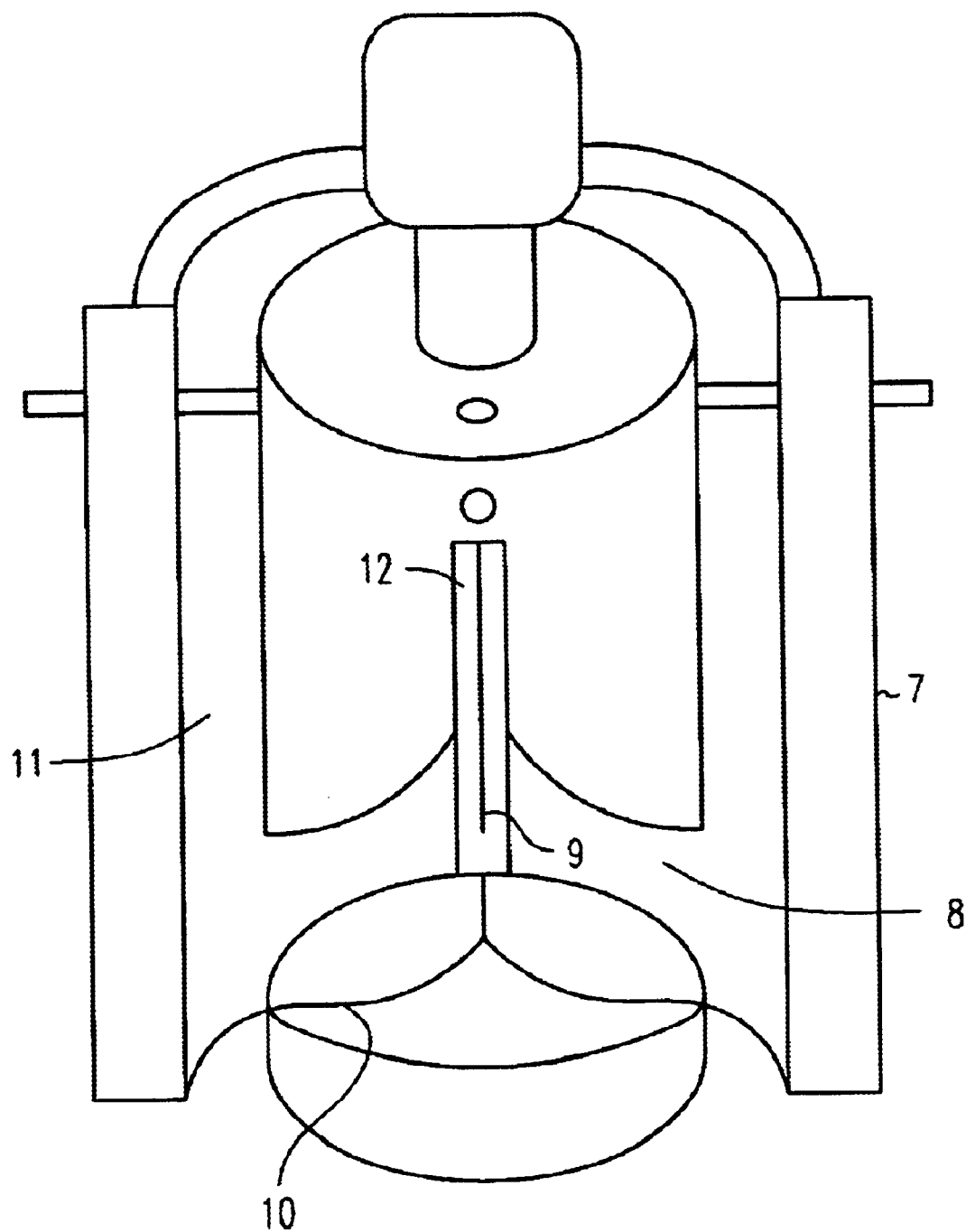
FIG. 13 illustrates an alternate embodiment of a valve equivalent mold. 7: cross-sectional view of a strut that maintains a gap between the top and bottom mandrel pieces.

Referring now to FIG. 13, there is illustrated an alternate embodiment of a VE mold wherein there is a central groove allowing for leaflet compaction and a coaptational surface. Struts maintain a gap between the top and bottom mandrel pieces. The gap between the mandrel and the wall defines the artificial aortic root/section of vein. Further, a divider wall separates individual leaflets. A gap between the top and bottom mandrel piece determines the geometry of the individual leaflets. Finally, a biopolymer gel is anchored at this edge to the artifical root. The resulting constrained cell-driven compaction of the gel results in commissure-to-commissure orientation.

According to this embodiment, the value of FIG. 13 is based on the idea of constraining surfaces which can induce alignment by simply being a barrier to gel compaction, rather than anchoring surfaces which can induce alignment by restricting gel compaction due to the network fibrils being entangled and thus anchored by the material comprising the surface; e.g., Velcro.

Set forth below is a bibliography of citations that are referred to hereinabove.

REFERENCES

1. J. M. Anderson, *J. Biomed, Mat. Res.*, 2 (1995).
2. G. W. Christie, *Eur. J. Caridothorac. Surg.*, 6, S25–32; discussion S33 (1992).
3. A. A. Sauren et al., *J. Biomech.*, 13, 97–104 (1980).
4. T. Shinoka et al., *Ann. Thorac. Surg.*, 60, S513–6 (1995).

5. N. L'Heureux, *J. Vasc. Surg.*, 17, 499–509 (1993).
6. V. H. Barocas et al., *J. Biomech. Eng.* (accepted) (1998).
7. V. H. Barocas et al., *J. Biomech. Eng.*, 119, 137–45 (1997).
8. T. S. Girton et al., *J. Biomed. Mat. Res.* (accepted) (1998).
9. A. A. Sauren et al., *J. Biomech.*, 16, 327–37 (1983).
10. R. Gottlob et al., *Venous Valves* (Springer-Verlag, 1986).
11. E. A. Talman et al., *J. Heart Valve Dis.*, 5, 152–9 (1996).

The following patents are hereby incorporated by reference in their entirety.

U.S. Pat. No. 5,770,417 issued to Vacanti et al. on Jun. 23, 1998

U.S. Pat. No. 5,759,830 issued to Vacanti et al. on Jun. 2, 1998

What is claimed is:

1. A molded valve leaflet comprising a molded biopolymer having fibrils and cells within the molded biopolymer, wherein the fibrils of the molded biopolymer have commisure-to-commisure alignment.

2. The molded valve leaflet of claim 1, wherein the biopolymer is cross-linked.

3. The molded valve leaflet of claim 2, wherein a stress-strain curve obtained using the molded valve leaflet is similar to a stress-strain curve obtained using a native valve leaflet.

4. The molded valve leaflet of claim 1, wherein the biopolymer is a fibrillar biopolymer.

5. The molded valve leaflet of claim 4, wherein the fibrillar biopolymer is collagen or fibrin.

6. The molded valve leaflet of claim 1, wherein the cells are fibroblasts or myofibroblasts.

7. The molded valve leaflet of claim 1, wherein the molded valve leaflet is a replacement for a native heart valve leaflet or a native venous valve leaflet.

8. A valve equivalent comprising a plurality of molded valve leaflets connected to a base, wherein the molded valve leaflets comprise a molded biopolymer having fibrils and cells within the molded biopolymer, wherein the fibrils of the molded biopolymer have commisure-to-commisure alignment.

9. The valve equivalent of claim 8, wherein the valve equivalent has 2, 3, or 4 molded valve leaflets connected to the base.

10. The valve equivalent of claim 8, wherein the biopolymer is cross-linked.

11. The valve equivalent of claim 10, wherein a stress-strain curve obtained using at least one of the molded valve leaflets is similar to a stress-strain curve obtained using a native valve leaflet.

12. The valve equivalent of claim 8, wherein the biopolymer is a fibrillar biopolymer.

13. The valve equivalent of claim 12, wherein the fibrillar biopolymer is collagen or fibrin.

14. The valve equivalent of claim 8, wherein the cells are fibroblasts or myofibroblasts.

15. The valve equivalent of claim 8, wherein the valve equivalent is a heart valve equivalent or a venous valve replacement.

* * * * *